(12) United States Patent
Carstens

(10) Patent No.: US 6,942,703 B2
(45) Date of Patent: Sep. 13, 2005

(54) PROSTHESIS

(75) Inventor: Johannes Carstens, Esslingen (DE)

(73) Assignee: Luisa Cerano GmbH, Nürtingen (DE)

( * ) Notice: Subject to any disclaimer, the term of this patent is extended or adjusted under 35 U.S.C. 154(b) by 0 days.

(21) Appl. No.: 10/485,392

(22) PCT Filed: Jul. 30, 2002

(86) PCT No.: PCT/EP02/08457
§ 371 (c)(1),
(2), (4) Date: Apr. 6, 2004

(87) PCT Pub. No.: WO03/013400
PCT Pub. Date: Feb. 20, 2003

(65) Prior Publication Data
US 2004/0158332 A1 Aug. 12, 2004

(30) Foreign Application Priority Data

Aug. 2, 2001 (DE) .......................................... 201 12 884
Nov. 20, 2001 (DE) .......................................... 201 18 926
May 3, 2002 (DE) .......................................... 202 07 046

(51) Int. Cl.[7] .................................................. A61F 2/80
(52) U.S. Cl. .......................................... 623/38; 623/32
(58) Field of Search ...................................... 623/27–38

(56) References Cited

U.S. PATENT DOCUMENTS

| | | | |
|---|---|---|---|
| 4,872,879 A | 10/1989 | Shamp | |
| 5,226,918 A | * 7/1993 | Silagy et al. | .................. 623/32 |
| 5,529,575 A | * 6/1996 | Klotz | ........................... 623/33 |
| 5,728,170 A | 3/1998 | Becker et al. | |
| 5,888,234 A | 3/1999 | Littig | |
| 5,931,872 A | 8/1999 | Lohmann | |
| 6,051,026 A | * 4/2000 | Biedermann et al. | ......... 623/38 |
| 6,106,559 A | 8/2000 | Meyer | |

FOREIGN PATENT DOCUMENTS

| | | |
|---|---|---|
| DE | 27 18 395 A | 11/1977 |
| JP | 8 089519 A | 4/1996 |

* cited by examiner

Primary Examiner—Bruce Snow
(74) Attorney, Agent, or Firm—Birch, Stewart, Kolasch & Birch, LLP

(57) ABSTRACT

The invention relates to prostheses for amputated patients. The shaft of the prosthesis has an outer shell and a concentric inner shell. Both shells are provided with longitudinal slits which are staggered in relation to each other and extend essentially in an axial direction. The diameter of the shaft of the prosthesis can be adjusted by tightening elements. An adaptor is fixed in the shaft of the prosthesis in such a way that the height of the adapter can be adjusted. A conical bearing surface for the stump of the limb is provided on the upper side of the adapter, a holding element for fixing an artificial limb is provided on the lower side of the same, and a coupling is provided inside the adapter for detachably fixing the coupling pin of a commercially available silicone liner.

23 Claims, 5 Drawing Sheets

PROSTHESIS

BACKGROUND OF THE INVENTION

1. Field of the Invention

The present invention relates to prostheses including a silicone liner with a coupling pin, a prosthesis shaft adapted to a limb stump, provided with longitudinal slits in portions thereof, the diameter being adjustable by tightening elements, and a holding device to connect artificial limbs with the shaft of the prosthesis.

2. Description of the Background Art

The purpose of prostheses is to replace, as best as possible, limbs that were lost through an accident or illness. To temporarily attach prostheses, for example artificial hands or feet, to a limb stump, special prosthesis shafts are used, which must be anatomically fitted to the limb stump. The attachment is commonly achieved by a vacuum between the prosthesis shaft and the limb stump or between the limb stump and a silicone liner.

Prosthesis shafts are made of metal, wood or cast resin. There are shafts of longitudinal or cross-oval shape, full-contact shafts, with a valve, or a silicone liner. With amputations below the knee joint, the prosthesis shafts are somewhat triangle-shaped, with support devices on the bone structure.

Since the prosthesis shafts must be fitted to the limb stump as exactly as possible, in order to generate and maintain the vacuum providing the firm attachment, the shafts are always custom-made products, which also must provide perfect pressure distribution of the load onto the entire stump area so that the stump can optimally transfer the body weight and other forces. Since initially after an accident or amputation, there is swelling of the limb stump within a few days or weeks, which then goes down again, but from a medical and orthopedic view, the patient should be fitted with a prosthesis as quickly as possible, at times several prosthesis shafts must be fabricated individually during the rehabilitation and adjustment period alone. This is unsatisfactory because of the expenditure of time and particularly money connected therewith.

It goes without saying that there has been no lack in attempts to rectify this situation. For example, inflatable air chambers have been arranged between the prosthesis shaft and the limb stump, see WO 00/23016. However, it was determined very quickly, that the grip attachment of the prosthesis to the limb stump was clearly reduced. In particular, the utilization value of the prosthesis was greatly reduced, since it is not solidly connected to the limb stump anymore.

To circumvent this problem, DE 27 18 395 C suggests filling air chambers with little balls. The ball-filled air chambers are supposed to adapt to the contours of the limb stump. By evacuating the air chambers, the balls are supposed to be molded into their actual, more or less well-adapted, position on the limb stump. Although it was good thinking, this construction did not prove itself and was not successful in practice.

From DE Patent 314 985, which was published in 1919, a prosthesis shaft is known, which is made of an inner and an outer shell. The inner and outer shell consists of individual lamellae, which are connected to each other by a rivet, in such a way that the diameter of the inner and out shell can be modified. To alter the diameter of the inner and outer shell, several tightening strings are provided. However, after closing the tightening strings for the outer shell, the tightening strings for the inner shell are no longer accessible, that is, their fasteners are not accessible anymore. Attaching and detaching of such a prosthesis shaft is, therefore, extremely cumbersome and time-consuming. In addition, prosthesis shafts made of lamellae cannot develop a vacuum for firm attachment to the limp stump.

A further, dual-shell prosthesis shaft is known from DE Patent 323 671, which was published in 1920. Here, too, an inner and outer shell consist of lamellae, whereby the lamellae of each shell are mutually connected by a rivet in such a way that it allows modification of the diameter with the help of tightening strips. Furthermore, an upper part of the lamellae of the inner shell are movably connected with the lamellae of the outer shell. The object of this construction is to avoid gaps between the individual lamellae. This construction also did not succeed in practice.

From the orthopedic practice it is known that limb stumps not only change in width but also in length. This is, for example, the case when the end of the limb stump, which is in direct contact with the prosthesis and, for example, in the case of an upper thigh prosthesis, must bear the entire body weight of the patient, gets infected and swelling occurs. A change in length can also occur when the swollen tissue is healing after an amputation or operation, and the swelling goes down. The limb stump then no longer sits correctly with a conical bearing surface that is provided in each prosthesis shaft and can, for example, no longer optimally transfer the body weight to the prosthesis. Also, in this case, new prosthesis shafts must be fabricated or the old prosthesis shafts must be modified. This is unsatisfactory.

From DE 82 16 840 U a prosthesis shaft is known, whereby a height of the conical bearing surface for the limb stump is adjustable. The height adjustment is done using level or wedge mechanics, which can be manipulated from the outside by the patient using a crank or something similar. Height adjustment with a built-in electric motor, possibly battery-operated, is also suggested. Since the height adjustment must be installed in the custom-made prosthesis shaft, it must be enlarged and modified accordingly. This increases the expenditure of time and money.

As previously mentioned, each prosthesis shaft must be fabricated in such a way that it transfers the forces optimal to the limb stump. To accomplish this, the prosthesis shaft must be suitably inflexible. In order to be able to adjust the diameter, the prosthesis shaft must be flexible. Flexibility directed towards the diameter can be achieved by construction with lamellae, as described in the German patents listed above. The connection between the lamellae with only one rivet, however, has the disadvantage that it weakens the stability of the prosthesis shaft.

SUMMARY OF THE INVENTION

It is therefore an object of the present invention to provide a prosthesis as previously described, which can be fabricated simply and thanks to prefabrication can be produced in greater series, cost-efficiently, having a great solidity and fits within predetermined limits to limb stumps, whereby a diameter and length can be changed.

The prosthesis includes: a silicone liner with a coupling pin; a prosthesis shaft that is fitted to a limb stump and provided with longitudinal slits in some areas, and is adjustable in diameter using tightening elements. A fastener is provided for connecting an artificial limb with the prosthesis shaft. The longitudinal slits are bridged over and the prosthesis shaft has a concentric band. Inside the band, a cylindrical adaptor is height-adjustably mounted. The adaptor has at its upper end a bearing surface for the limb stump or an end of the silicone liner and a fastener at the bottom, and on its inside a coupling for detachable fixation of the coupling pin at the top and mechanics for loosening the coupling at the bottom.

According to the present invention, the flexibility of the prosthesis shaft is achieved by the longitudinal slits, the inflexibility of the slitted prosthesis shaft by bridging the longitudinal slits. Thanks to the considerably improved stiffness, the wall strength can be decreased and thus, comfort of wearing can be increased. The adjustability of the diameter of the prosthesis shaft makes it possible, through industrial prefabrication of only a few basic models for the right and the left side of the body, respectively, to meet the demand for most of the common initial provisions. Moreover, the prosthesis can be attached and detached quickly and comfortably. Its fit is impeccable.

To attach the prosthesis, the silicone liner is first rolled over the limb stump. Next, the limb stump and silicone liner must be inserted into the prosthesis shaft of the prosthesis, until the end of the limb stump or the silicone liner rests on the conical bearing surface, whereby the coupling pin is completely immersed in the coupling. When the prosthesis shaft fits very tightly, for example, because the limp stump is slightly swollen, it can happen with a one-piece prosthesis shaft that the optimal position is not achieved. For this reason, current commercial prostheses have an installed freewheeling gear wheel, which the wearer of the prosthesis can manipulate from the outside with a coin. This gear wheel interacts with the profiled coupling pin, which in this way is pulled into the prosthesis shaft. In contrast thereto, with the prosthesis of the present invention, such a construction is entirely superfluous, because any limb stump can be inserted into the open prosthesis shaft without any difficulty. The same is true for the detachment of the prosthesis.

As soon as the patient no longer needs the interim prosthesis of this invention, it can be cleaned and used for the next patient. The reduction of resources and expenses connected therewith is, to date, unmatched.

The ability to industrially prefabricate the interim prosthesis of the invention in few sizes is, by the way, only possible because the prosthesis of this invention not only has a width adjustment but also a length adjustment in the form of a cylindrical adaptor, which is inserted, more or less as needed, into the prosthesis shaft. This adaptor has, at its top, the conical bearing surface for the limb stump, at its bottom the standard coupling for fastening an artificial limb, and on its inside the mechanics for detachably fastening the coupling pin and commercial silicone liner.

According to a first embodiment of the invention, the longitudinal slits are at least partially bridged, e.g., spanned, with a flexible material, which forms ripples and folds. These ripples and folds can be made of the same material that the prosthesis shaft is made of, whereby the flexibility is achieved by careful selection of wall strength and shape.

As an alternative, there is the possibility to bridge the longitudinal slits with a rubber-like material, in particular silicone rubber.

In a preferred embodiment of the invention, the prosthesis shaft is formed by two concentric shells. Therewith, an inner area of the outer shell is essentially the same as an outer area of the inner shell, the longitudinal slits of the outer and inner shells are staggered in relation to each other, and the diameter of both shells is mutually adjustable by tightening elements. Additionally, the inner and outer shells have a concentric band, which holds the adaptor.

This embodiment of the invention has a great stiffness, together with low weight and high comfort in wearing, even with minimal wall strengths of the shells, which fit each other perfectly, comparably to the skins of an onion. Since both shells are held in place by one type of tightening element, such a prosthesis is very quickly attached and detached. Furthermore, this embodiment of the invention can be industrially prefabricated with a few basic models, which reduces the cost of the prosthesis even further.

According to an advantageous embodiment of the invention, the coupling pin on the silicone liner is a plain cylinder, and the coupling includes a clamping plate and an opening that fits the coupling pin, whereby the clamping plate is pivotably positioned on an axis and is pivoted into a clamp position by springs. Such a smooth coupling pin is not only simpler and more cost-effective than a profiled coupling pin, but is also in all cases easy to detach, as opposed to conventional profiled pins, which are held by a free-wheeling gear wheel, which after prolonged wearing of the prosthesis is under enormous pre-stress and tends to jam.

Advantageously, the clamping plate, which is positioned in the upper part of the adapter because of the shortness of the coupling pin, is connected by a rope or a spoke to a manual lever, which is positioned at the lower end of the adapter and is thus easily accessible at every height adjustment. Basically, this coupling construction also works with the commercial profiled coupling pins, however, the height adjustment is then not progressive.

Advantageously, the adapter includes two parts, which are held together by screws or the like. In an advantageous embodiment, one of the fastening screws can be simultaneously used as a pivotal axis for the clamping plate of the coupling.

The connection between the inner and outer shells and the adapter is preferably performed with a clamp connection. In order to achieve a safe clamp connection between the prosthesis shaft and the adapter it is suggested to slit the band elastically.

In a preferred embodiment, the clamp ring itself has a flange for mounting the tightening screws.

As mentioned, the adaptor of this invention allows adaptation to limb stumps of varying lengths or to those that had to be shortened for medical reasons, without having to change the actual prosthesis shaft. Only the connection rod between the artificial limb and the conventional fastener, which is positioned at the lower end of the adapter, has to be extended.

According to an embodiment of the invention, the mechanics for detaching the coupling includes a manual lever, which is retractable, so that it does not get in the way when the prosthesis is being worn.

Advantageously, the shells of the prosthesis shaft are made of fiber-reinforced, particularly carbon fiber-reinforced, plastic, whereby the reinforced fibers essentially extend in an axial direction so that, as desired, there is a high stiffness in an axial direction and sufficient flexibility in a circumferential direction.

In a case, where the longitudinal slits in the outer or inner shell bother the patient, these can, at least partially, be filled with a flexible material. This flexible material can be a rubber-like substance, for example, silicone rubber.

In order to be able to attach and detach the prosthesis of the invention very quickly, the tightening element is preferably a tightening band with a toggle latch closure.

To prevent vascular congestion in the limb stump because the tightening band is too tight, or because the prosthesis does not fit-properly because the tightening band is not tight enough, the tightening element is equipped with a length adaptation device, which is to be operated only by an expert, for example, an orthopedic technician. Thus, the patient can only open and close the tightening element.

Lastly, one should make sure that inner shell and outer shell, adapter, and in some cases, clamp ring are safeguarded against twisting.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
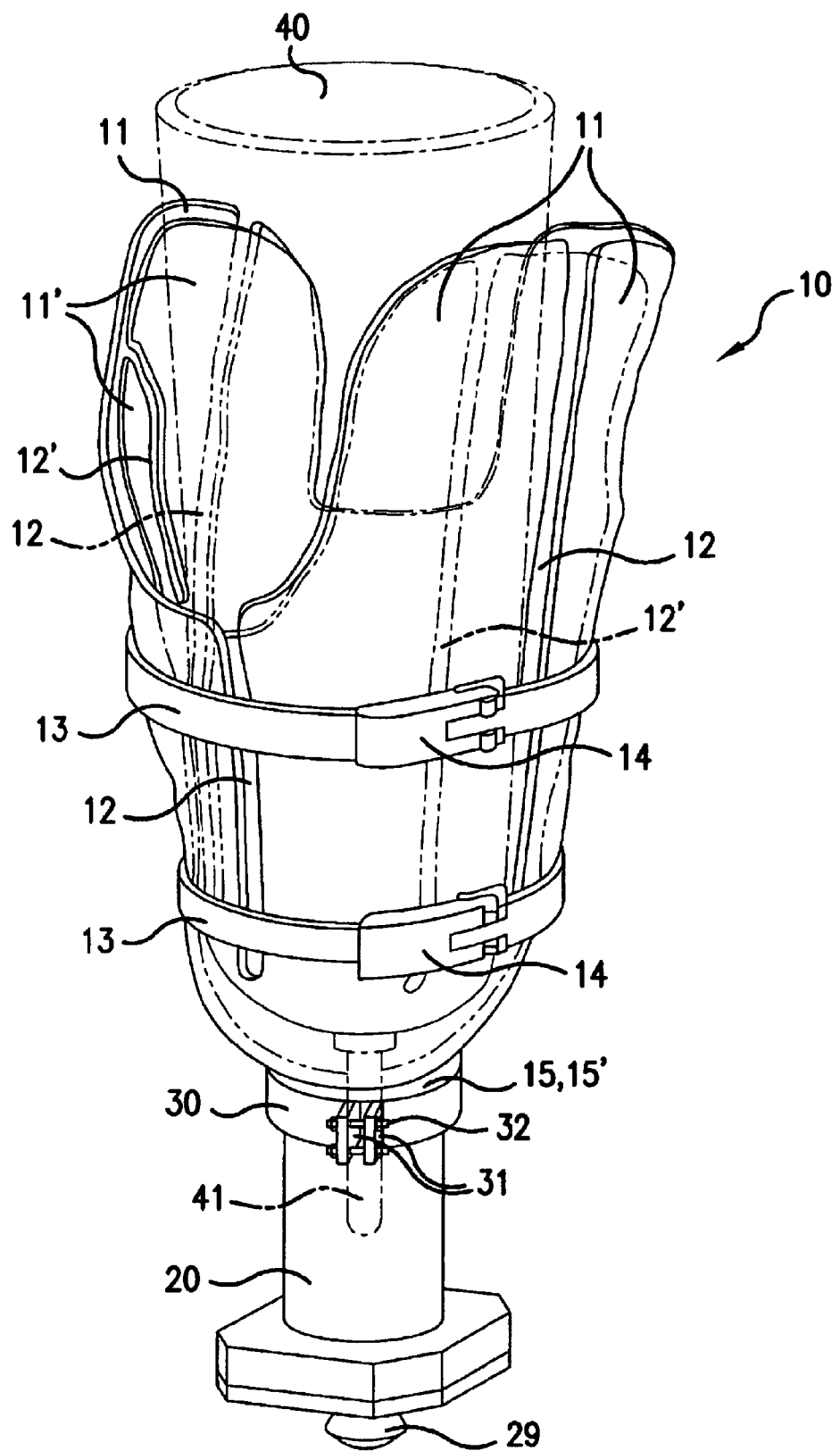
FIG. 1 is a prosthesis shaft according to a preferred embodiment of the present invention, which is adjustable in a circumferential and a longitudinal direction.

FIG. 1 is a perspective illustration of a prosthesis shaft 10, which is anatomically fitted to a limb stump (not shown), at the bottom of which, a coupling 29, e.g., a holding element, is mounted to which, if need be, an artificial limb, for example an arm or foot prosthesis, can be attached via an extension rod.

The prosthesis shaft 10 includes an outer shell 11 and an inner shell 11'. In the outer and inner shells 11, 11', there are slits 12, 12' extending essentially in an axial direction, which are staggered in relation to each other. In an ideal situation, the outer and inner shell 11, 11' touch each other like the skins of an onion.

When the outer and inner shell 11, 11' is made of a carbon fiber-reinforced plastic, thinner walls and thus reduced weight can be achieved. If the reinforced fibers extend mostly in an axial direction, the shells 11, 11' are inflexible in a longitudinal direction, and flexible in a circumferential direction.

In order to be able to adjust the diameter of the prosthesis shaft 10 having the outer and inner shells 11, 11', two tightening bands 13 including toggle catch closures 14 are provided, the width of which can be adjusted by a precision-adjuster (not illustrated) by a trained technician. When the toggle catch closures 14 are closed, the slits 12, 12' are compressed, which causes a tight fit of the prosthesis shaft 10 to the limb stump.

FIG. 1 also illustrates, purely schematically, a silicone liner 40. Initially, this is put over the limb stump and fixedly attached by vacuum. On the underside of the silicone liner 40, there is provided a coupling pin 41, which interacts with a coupling. This coupling is located inside a cylinder-shaped adapter 20, which is fixated height-adjustably in the prosthesis shaft 10 with the aid of a clamp ring 30. For this purpose, the outer and inner shell 11, 11' each have at their lower end a concentric band 15, 15'. Thanks to a slit 16, the band 15, 15' is elastically flexible. The clamp ring 30 has a flange 31 and can be tightened and/or loosened by tightening screws 32.

Figure 2:
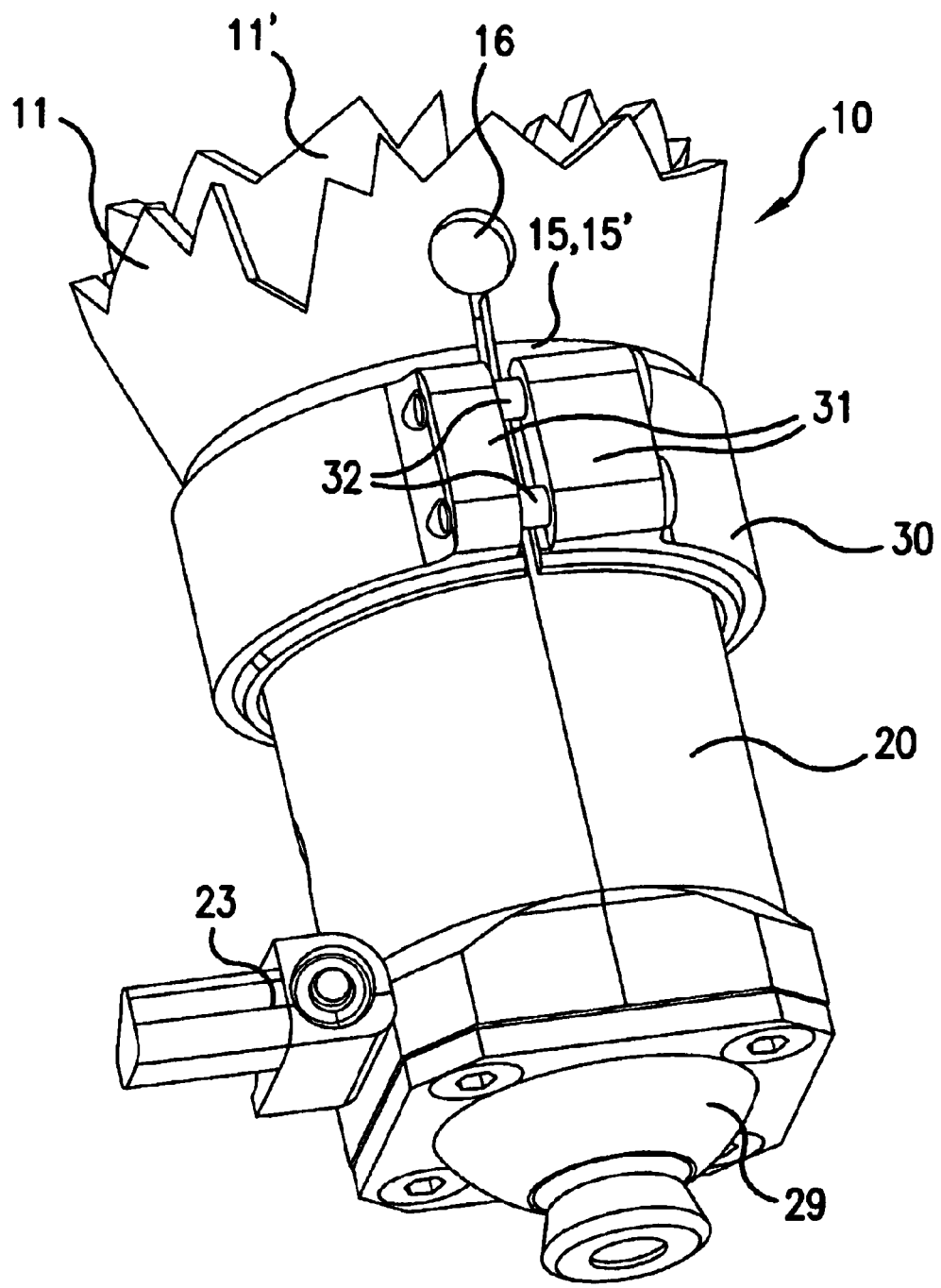
FIG. 2 is part of the prosthesis shaft of FIG. 1 in enlarged scale, with an inserted adapter in a fully extended position.

FIG. 2 shows, in an enlarged scale, a section of FIG. 1. The adapter 20 can be seen in a completely extended condition. Furthermore, at the lower end of the adapter 20, a foldable manual lever 23 can be seen, with which the coupling located in adapter 20 can be operated. Further details will be described with the description of FIG. 4.

Figure 3:
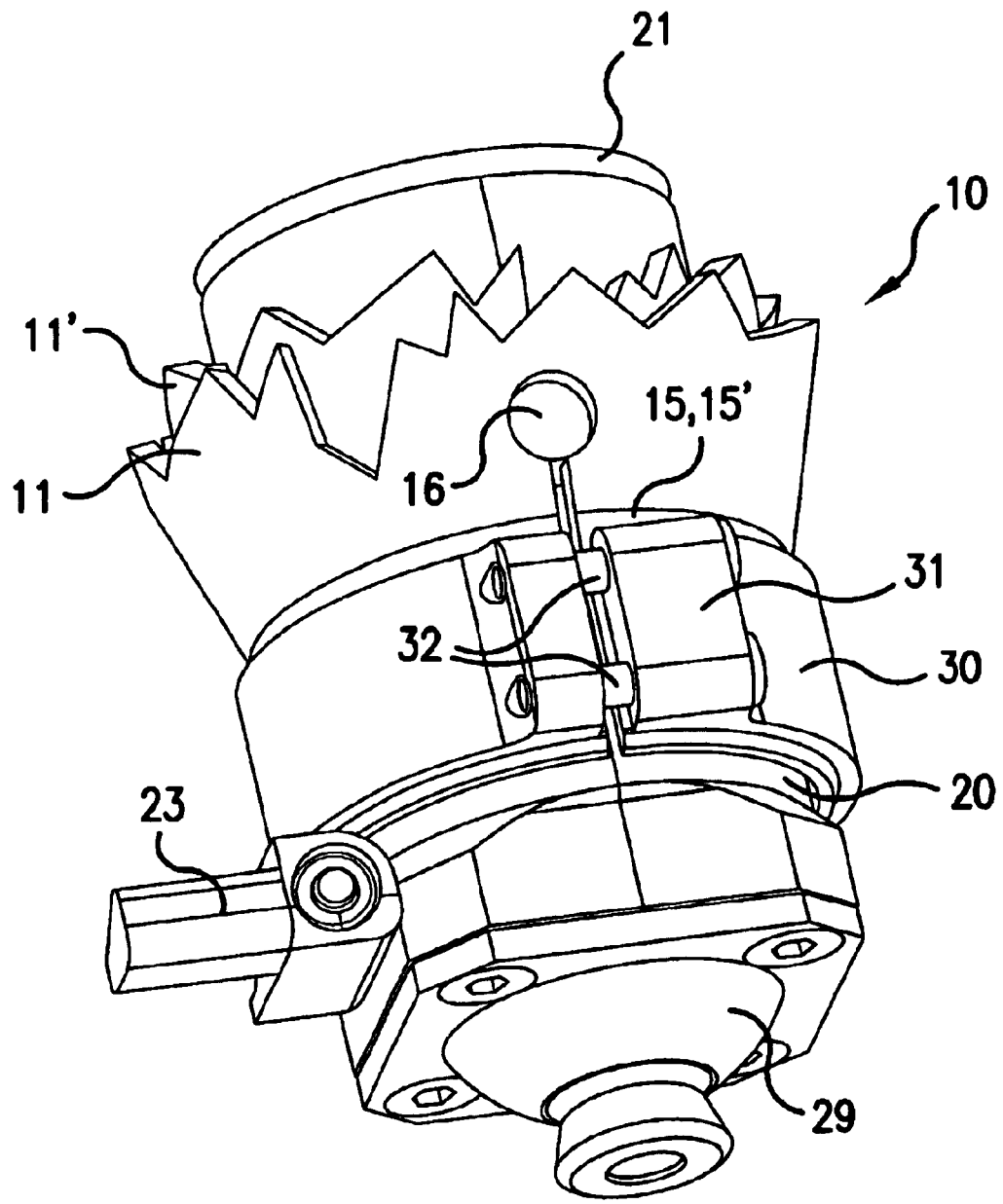
FIG. 3 is the adapter of FIG. 2 in a fully immersed position.

FIG. 3 shows the adapter of FIG. 2 immersed completely in the prosthesis shaft 10. Thus, at the upper end of the adapter 20, a conical bearing surface 21 for the limb stump, that is, the silicone line 40, can be seen.

Figure 4:
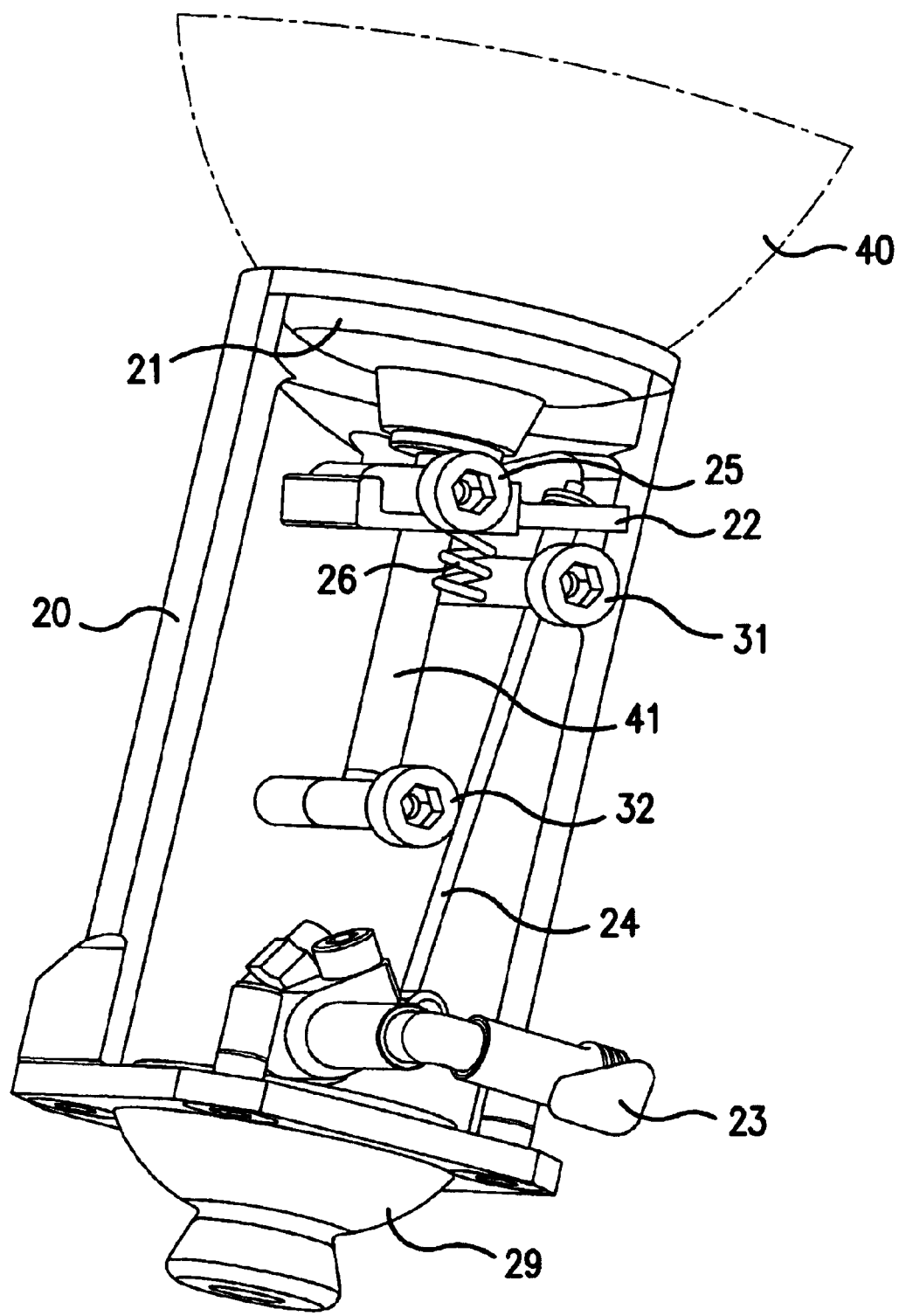
FIG. 4 is the adapter of FIG. 2 and 3 in an opened position.

FIG. 4 shows the adapter 20 in an opened position. At its top, one can see the conical bearing surface 21, on which the top of the silicone 40 rests. Its coupling pin 41 is formed as a smooth cylinder and extends through the bearing surface 21. The coupling includes a clamp plate 22, which is pivotably positioned around an axis 25, and which simultaneously serves as a connection screw. Springs 26 pivot the clamp plate 22 into a clamp position so that the coupling pin 41 can be inserted without a problem and at the same time is safeguarded against unintended detachment. Additional screws 31, 32 connect parts of the adapter 20.

To detach the clamp plate 22, the manual lever 23 is used, which is connected with the clamp plate 22 via a coupler rod 24 and/or a coupler rope located inside the adapter 20. When the patient moves the lever 23 downward, the clamp plate 22 is pivoted downward from its clamp position, as illustrated in the drawing, to a neutral position, and the patient is able to remove the coupling pin 41 with silicone liner 40 and limb stump from the adapter 20 and/or prosthesis shaft 10, as soon as the tightening bands 13, 14 are opened. The clamp plate 22 is an ordinary, hardened steel plate with a bore, which corresponds with the diameter of the coupling pin 41. This simple construction is extremely durable and safe to operate.

Figure 5:
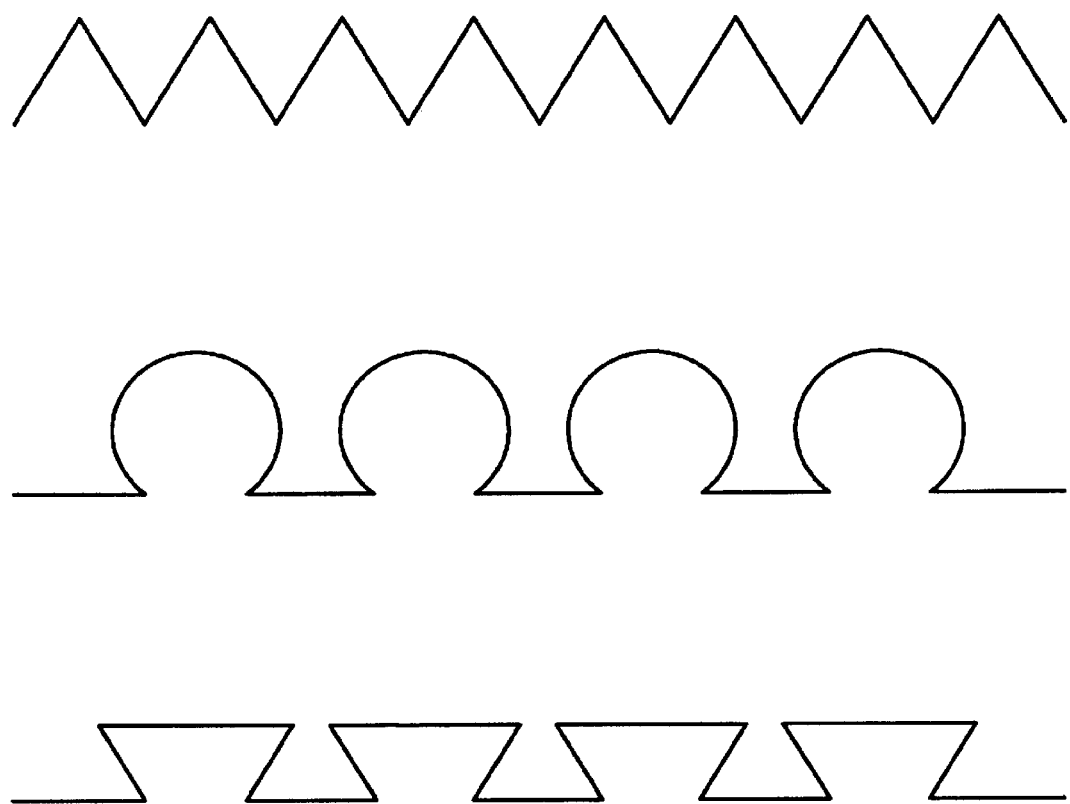
FIG. 5 shows various cross-sections of folds or ripples.

FIG. 5 shows, purely schematically, three possible cross-sections of folds and/or ripples, with which the longitudinal slits 12 can be bridged, e.g., spanned. These cross-sections are, seen from top to bottom, of zig-zag, omega and dovetail shape. In other words, edge surfaces of the outer and inner shells 11, 11', which are formed by the span of the longitudinal slits 12, 12', have a cross-section as shown in FIG. 5.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A prosthesis comprising:
   a silicone liner having a coupling pin;
   a prosthesis shaft for being fitted to a limb stump and provided with longitudinal slits in a portion thereof, the prosthesis shaft being adjustable in diameter by tightening elements; and
   a holding element for connecting an artificial limb with the prosthesis shaft, wherein the prosthesis shaft has a concentric band circumferentially attached thereto, the concentric band having a cylindrical adapter height-adjustably installed therein, wherein the adapter includes a bearing surface at an upper end thereof for receiving the limb stump or the end of the silicone liner and a holding element at a lower end, and wherein the adapter includes in an interior portion a coupling for detachably securing of the coupling pin at the upper end and mechanics for detaching the coupling.

2. The prosthesis according to claim 1, wherein edge surfaces of the prosthesis shaft that are formed by the longitudinal slits are at least partially spanned by a flexible material, which forms ripples or folds.

3. The prosthesis according to claim 1, wherein:

the prosthesis shaft is formed by an inner shell and an outer shell that are concentric, an inner surface of the outer shell is essentially the same as an outer surface of the inner shell, the longitudinal slits of the outer and inner shells are staggered in relation to each other, the diameter of the inner and outer shells are mutually adjustable by a tightening element, and the outer and inner shells contain the concentric band.

4. The prosthesis according to claim 3, wherein the inner and outer shells are made of fiber-reinforced plastic.

5. The prosthesis according to claim 4, wherein the reinforced fibers extend essentially in an axial direction.

6. The prosthesis according to claim 4, wherein the fiber-reinforced plastic is carbon fiber-reinforced plastic.

7. The prosthesis according to claim 3, wherein the longitudinal slits in the outer shell and/or the inner shell are at least partially bridged by a rubber-like material.

8. The prosthesis according to claim 7, wherein the rubber-like material is silicone rubber.

9. The prosthesis according to claim 3, wherein the inner shell, the outer shell, the adapter, and the clamp ring are safeguarded against contortion.

10. The prosthesis according to claim 1, wherein:

the coupling pin is a smooth cylinder, and wherein the coupling comprises:

a clamp plate with an opening, which is fitted for the coupling pin;

an axis, on which the clamp plate is pivotally positioned; and springs, which pivot the clamp plate into a clamp position.

11. The prosthesis according to claim 10, wherein the adapter includes two parts, and wherein the axis simultaneously serves as a connection element.

12. The prosthesis according to claim 10, wherein the mechanics for detaching the coupling include a manual lever, and wherein the manual lever is foldable.

13. The prosthesis according to claim 1, wherein the concentric band is elastically slitted.

14. The prosthesis according to claim 1, wherein a clamp ring is mounted onto the concentric band.

15. The prosthesis according to claim 14, wherein the clamp ring has a flange for mounting clamp screws.

16. The prosthesis according to claim 1, wherein the tightening element has a tightening band with a toggle latch closure.

17. The prosthesis according to claim 1, wherein the tightening element has a length adjustment.

18. The prosthesis according to claim 17, wherein the tightening element is manually operable.

19. The prosthesis according to claim 1, wherein the tightened by the tightening elements.

20. A prosthesis comprising:

a prosthesis shaft for receiving a limb stump, the prosthesis shaft including an inner shell and an outer shell that has longitudinal slits provided therein for enabling a diameter adjustment of the prosthesis shaft about the limb stump; and an adapter being height adjustably and securely attached to the prosthesis shaft at an upper end of the adapter, the adapter having a holding element provided on a lower end for attachably receiving an artificial limb, and the adapter having a coupling for releasably securing a coupling pin, the coupling pin being connectable to the limb stump.

21. The prosthesis according to claim 20, wherein a tightening band, which is provided substantially circumferentially about the prosthesis shaft, enables the diameter adjustment.

22. The prosthesis according to claim 20, wherein the height of the adapter, in relation to the prosthesis shaft, is adjusted by an adaptive securing of the adapter via an adjustable concentric band that is fixedly provided on the prosthesis shaft.

23. The prosthesis according to claim 20, wherein the pin is connectable to the limb stump by a silicon liner.

* * * * *